(12) United States Patent
Neuenschwander

(10) Patent No.: US 8,362,159 B2
(45) Date of Patent: *Jan. 29, 2013

(54) DEGRADABLE BIOCOMPATIBLE BLOCK COPOLYMER

(75) Inventor: Peter Neuenschwander, Baden (CH)

(73) Assignee: Eidgenossische Technische Hochschule Zurich, Zurich (CH)

( * ) Notice: Subject to any disclaimer, the term of this patent is extended or adjusted under 35 U.S.C. 154(b) by 0 days.

This patent is subject to a terminal disclaimer.

(21) Appl. No.: 12/940,786

(22) Filed: Nov. 5, 2010

(65) Prior Publication Data

US 2011/0093066 A1 Apr. 21, 2011

Related U.S. Application Data

(63) Continuation of application No. 10/564,360, filed as application No. PCT/EP2004/007344 on Jul. 6, 2004, now abandoned.

(30) Foreign Application Priority Data

Jul. 16, 2003 (EP) ..................... 03016148

(51) Int. Cl.
*C08G 63/08* (2006.01)
(52) U.S. Cl. .................... 525/450; 528/359; 528/354
(58) Field of Classification Search ............. 525/437
See application file for complete search history.

(56) References Cited

U.S. PATENT DOCUMENTS

| 4,210,730 A | 7/1980 | Hirzy |
| 4,212,957 A | 7/1980 | Hirzy |
| 4,273,890 A | 6/1981 | Hirzy |
| 4,281,077 A | 7/1981 | Hirzy |
| 4,826,945 A | 5/1989 | Cohn et al. |
| 5,124,371 A * | 6/1992 | Tokiwa et al. ............ 523/124 |
| 5,352,763 A | 10/1994 | Yamaguchi et al. |
| 5,665,831 A | 9/1997 | Neuenschwander et al. |
| 5,840,811 A * | 11/1998 | Hori et al. ............ 525/411 |
| 6,548,569 B1 * | 4/2003 | Williams et al. ............ 523/124 |

FOREIGN PATENT DOCUMENTS

| DE | 42 24 401 A1 | 1/1994 |
| EP | 0 038 392 A1 | 10/1981 |
| EP | 0 295 055 A2 | 12/1988 |
| EP | 0 552 896 A1 | 7/1993 |
| EP | 0 696 605 A1 | 2/1996 |
| EP | 1 314 749 A2 | 5/2003 |
| JP | 05-295075 A | 11/1993 |

(Continued)

OTHER PUBLICATIONS

Hori et al. Ring-Opening Copolymerization of Optically Active b-Butyrolactone with Several Lactones Catalyzed by Distannoxane Complexes: Synthesis of New Biodegradable Polyesters. Macromolecules 1993,26, 4388-4390.*

(Continued)

*Primary Examiner* — Randy Gulakowski
*Assistant Examiner* — Mike M Dollinger
(74) *Attorney, Agent, or Firm* — Oliff & Berridge, PLC

(57) ABSTRACT

Disclosed is a biocompatible block copolymer containing the polycondensation product of a diol and an additional component selected from the group of the same diol, an $\alpha,\omega$-dihydroxy-polyester or an $\alpha,\omega$-dihydroxy-polyether. Also disclosed are a medical implant containing the block copolymer, the use of said block copolymer for the production of a medical implant, a diol and a method for the production thereof. The diol may be obtained by transesterification of $\alpha,\omega$-dihydroxy-[(oligo(3-(R)-hydroxybutyrate)-ethylene-oligo-(3-(R)-hydroxybutyrate)] with diglycolide. Transesterification is carried out, preferably, in the presence of a catalyst.

19 Claims, 2 Drawing Sheets

DECREASE IN THE MOLECULAR MASS OF THE FOAM AS A FUNCTION OF STORAGE IN WATER

△ POLYMER WITH TREND LINE

□ REFERENCE POLYMER WITH TREND LINE

| | FOREIGN PATENT DOCUMENTS | | |
|---|---|---|---|
| JP | 10-046013 A | 2/1998 | |
| JP | 10-237166 A | 9/1998 | |
| WO | WO 98/29470 | 7/1998 | |

OTHER PUBLICATIONS

International Search Report for International Application No. PCT/EP2004/007344, mailed Nov. 26, 2004.

Lendlein, A., et al., Abstract of "Hydrolytic Degradation of Phase-Segregated Multiblock Copoly(ester urethane)s Containing Weak Links," published online on Sep. 5, 2001.

Lendlein, A., et al., Abstract of "Tissue-compatible Multiblock Copolymers for Medical Applications, Controllable in Degradation Rate and Mechanical Properties," published online on Dec. 16, 1998.

* cited by examiner

DECREASE IN THE MOLECULAR MASS OF THE
FOAM AS A FUNCTION OF STORAGE IN WATER

△ POLYMER WITH TREND LINE

☐ REFERENCE POLYMER WITH TREND LINE

DECREASE IN THE MOLECULAR MASS OF THE
POWDER AS A FUNCTION OF STORAGE IN WATER

△ POLYMER WITH TREND LINE

□ REFERENCE POLYMER WITH TREND LINE

DEGRADABLE BIOCOMPATIBLE BLOCK COPOLYMER

CROSS-REFERENCE TO RELATED APPLICATIONS

This is a Continuation of application Ser. No. 10/564,360 filed Mar. 2, 2006, which in turn is a National Phase of Application No. PCT/EP2004/0073444 filed Jul. 6, 2004, which claims the benefit of European Patent Application No. 03 016 148.3 filed Jul. 16, 2003. The disclosure of the prior applications is hereby incorporated by reference herein in their entirety.

BACKGROUND

The invention relates to a biocompatible block copolymer comprising the polycondensation product of a diol and of a further component selected from the group of the same diol, an α,ω-dihydroxypolyester or an α,ω-dihydroxypolyether. The invention additionally relates, besides the conventional applications of polyurethanes, to a medical implant comprising the block copolymer, to the use of the block copolymer for producing a medical implant, and to a diol and the process for preparing the same. Wherever the term medicine is used, both human and veterinary medicine is meant thereby.

The number of biocompatible polymers employed in practice for medical implants is surprisingly small. This is attributable, apart from the problem of compatibility, firstly to the great technical requirements in relation to mechanical strength, sterilizability, biodegradability and secondly to the large number of different administrative regulations in individual countries. The biodegradability of such a polymer in particular poses exacting requirements because the desired rate of degradability depends greatly on the use.

EP 0 196 486 discloses a biocompatible block copolymer that can be used as medical implant. This block copolymer has a crystalline and an amorphous component. The degradability of these block copolymers is, however, not fast enough for all applications.

SUMMARY

It is an object of the present invention to provide a novel polymer with faster degradability and negligibly altered biological properties.

An additional object of the present invention is to provide a polymer which is readily degradable outside the body.

This object is achieved by the block copolymer as claimed in claim 1. Preferred embodiments of the invention are described in claims 2-18 and in the description.

These and other features and advantages of various exemplary embodiments of materials, devices, systems and/or methods are described in or are apparent from the following detailed description.

DETAILED DESCRIPTION OF EMBODIMENTS

Figure 1:
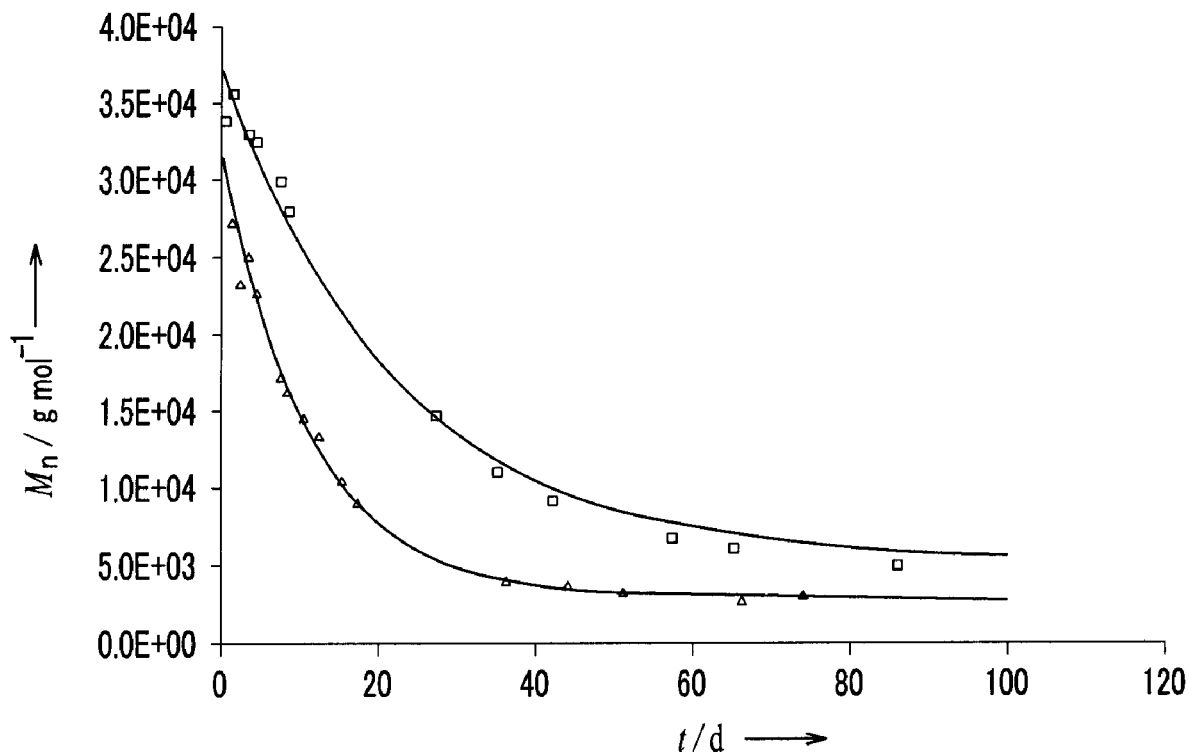
FIGS. 1 and 2 are graphical representations of decrease in molecular mass as a function of storage in water.

It has been found that the biocompatible block copolymer and the diol have an exceptionally good biocompatibility. In addition, it is possible through the incorporation of the glycolide or diglycolide units to control the hydrolytic and biological rate of degradability of the biocompatible block copolymer of the invention and of the diol. The degradability of the block copolymer of the invention outside the body can be increased, besides the incorporation of glycolide or diglycolide units, by (L,L)-dilactide, (D,D)-dilactide, (D,L)-dilactide or mixtures thereof. Since the diol is composed of α- and/or β-hydroxyalkanoates, degradation thereof forms toxicologically unobjectionable metabolites. There is intermediate formation of solid particles that are relatively small and are eliminated from the body by phagocytosis. The size of the water-insoluble particles is reduced through the incorporation of the diglycolide or glycolide units, thus facilitating and expediting the phagocytosis of the particles. Applications in the non-medical sector are, for example, packaging materials and building material.

Incorporation of the diol into the block copolymers of the invention makes it possible to influence the rate of degradation of the crystalline component. The degradability in the body is controlled only through the incorporation of the glycolide or diglycolide units. It is therefore possible to control the degradability of such block copolymers via the crystalline component alone, the amorphous component alone or both components together.

The block copolymer of exemplary embodiments of the invention can be obtained by linear polycondensation of a diol with a further component selected from the group of the same diol, an α,ω-dihydroxypolyester or an α,ω-dihydroxypolyether in the presence of diisocyanate, diacid halide or phosgene. Linkage of these components results in polyurethanes with diisocyanate, polyesters with diacid halide and polycarbonates with phosgene.

The diol (1) can be obtained by transesterification of α,ω-dihydroxy[oligo(3-(R)-hydroxybutyrate)ethylene-oligo(3-(R)-hydroxybutyrate)] (2), which is referred to hereinafter as PHB diol, with diglycolide (3) dilactide or caprolactone or mixtures thereof, the transesterification preferably being carried out in the presence of a catalyst. In the following reaction scheme, m is 1 to 50, n is 1 to 50, x+y is 1 to 50.

When diglycolide is incorporated, the resulting polymers have a high rate of degradability in the body, whereas dilactide and caprolactone units have no influence thereon.

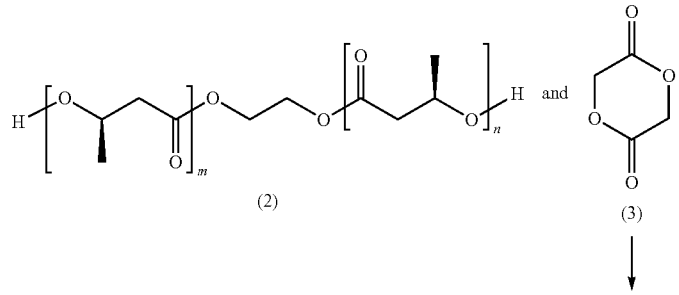

(2)          (3)

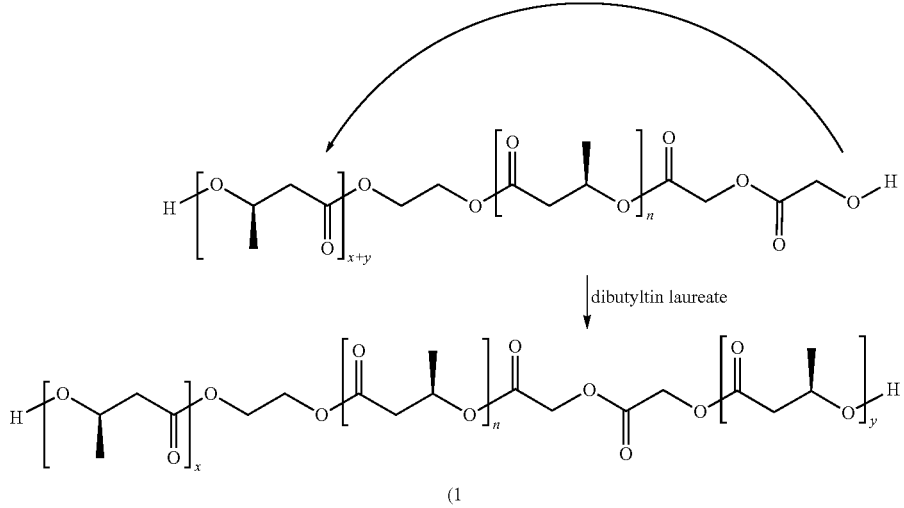

(1)

Preferred catalysts are transesterification catalysts in particular based on tin, e.g. dibutyltin dilaurate. The diol preferably has a molecular weight of from 500 to 10 000 daltons. The diol (1) preferably has a total glycolide content of up to 40 mol %, particularly preferably up to 30 mol %. A preferred diol of exemplary embodiments of the invention is α,ω-dihydroxy[oligo(3-(R)-hydroxybutyrate)-stat-glycolide)ethylene-oligo(3-(R)-hydroxybutyrate-stat-glycolide)] or the corresponding stat-lactide or stat-caprolactate compounds if dilactide or caprolactone is used instead of diglycolide.

An α,ω-dihydroxypolyester can be obtained for example by transesterification of poly[(R)-(3)-hydroxybutyric acid] or its copolymers with 3-hydroxyvaleric acid with ethylene glycol.

Further suitable α,ω-dihydroxypolyesters are oligomers of α-, β-, γ- and ω-hydroxy carboxylic acids and their cooligomers which are obtained by ring-opening polymerization of cyclic esters or lactones. Preferred cyclic esters of this type are (L,L)-dilactide, (D,D)-dilactide, (D,L)-dilactide, diglycolide or the preferred lactones such as β-(R)-butyrolactone, β-(S)-butyrolactone, β-rac-butyrolactone and ε-caprolactone or mixtures thereof. The ring opening takes place with aliphatic diols such as ethylene glycol or longer-chain diols. The molecular weight of the resulting macrodiol is determined by the stoichiometrically employed amount of these diols.

The ring-opening polymerization of the cyclic esters or lactones preferably takes place without diluent in the presence of a catalyst, for example SnO(Bu)$_2$ at 100° C. to 160° C. The resulting macrodiols have molecular weights of about 300-10 000 daltons. The macrodiols prepared from mixtures of cyclic esters or lactones have a microstructure which depends on the amount of catalyst and which is statistical or alternating in the distribution of the monomeric components between block form. The distributions statistics have an influence on the physical properties. Examples of such esters which are obtained by ring-opening polymerization of cyclic esters and lactones in the presence of a catalyst and which can be used to prepare the block copolymers are α,ω-dihydroxy-[poly(L-lactide)-ethylene-poly(L-lactide)]; α,ω-dihydroxy-[oligo(3-(R)-hydroxybutyrate-ran-3-(S)-hydroxybutyrate)-ethylene-oligo(3-(R)-hydroxybutyrate-ran-3-(S)-hydroxybutyrate)]; α,ω-dihydroxy-[oligo(glycolide-ran-ε-caprolactone)-ethylene-oligo(glycolide-ran-ε-caprolactone)]; α,ω-dihydroxy-[oligo(L)-lactide-ran-ε-caprolactone)-ethylene-oligo(L)-lactide-ran-ε-caprolactone)]; α,ω-dihydroxy-[oligo(L)-lactide-ran-glycolide)-ethylene-oligo(L)-lactide-ran-glycolide)]; α,ω-dihydroxy-[oligo(3-(R)-hydroxybutyrate-ran-3-(S)-hydroxybutyrate-ran-glycolide)-ethylene-oligo(3-(R)-hydroxybutyrate-ran-3-(S)-hydroxybutyrate-ran-glycolide)]; α,ω-dihydroxy-[oligo-3-(R)-hydroxybutyrate-ran-3-(S)-hydroxybutyrate-ran-L-lactide-ethylene-oligo(3-(R)-hydroxybutyrate-ran-(S)-hydroxybutyrate-ran-L-lactide)] and α,ω-dihydroxy-[oligo(3-(R)-hydroxybutyrate-ran-3-(S)-hydroxybutyrate-ran-ε-caprolactone)ethylene-oligo(3-(R)-hydroxybutyrate-ran-3-(S)-hydroxybutyrate-ran-ε-caprolactone)].

The ring-opening polymerization for preparing these macrodiols can also take place without catalyst. Diisocyanates suitable for preparing the polyurethane variant of the block copolymers are in particular hexamethylene diisocyanate, 2,2,4-trimethylhexa-methylene diisocyanate, cyclohexyl 1,4-diisocyanate, cyclohexyl 1,2-diisocyanate, isophorone diisocyanate, methylenedicyclohexyl diisocyanate and L-lysine diisocyanate methyl ester.

Diacid halides particularly suitable for preparing the polyester variant of the block copolymers are those of oxalic acid, malonic acid, succinic acid, glutaric acid, adipic acid, pimelic acid, suberic acid, azelaic acid, trimethyladipic acid, sebacic acid, dodecanediacid, tetradecanedioic acid and hexadecanedioic acid.

Reaction to give the polymer of exemplary embodiments of the invention takes place almost quantitatively. It has moreover been found that incorporation of the dilactide, diglycolide and/or caprolactone units results in the polymers of exemplary embodiments of the invention being soluble in methylene chloride. It is thus possible to remove impurities by filtration. A cost-effective process with which the polymer of exemplary embodiments of the invention can be prepared with high purity is provided thereby.

A particularly preferred block copolymer is poly[poly[α,ω-dihydroxy-[(oligo(3-(R)-hydroxybutyrate)-stat-glycolide)-ethylene-oligo-(3-(R)-hydroxybutyrate-stat-glycolide)]alt-2,2,4-trimethylhexamethylene 1,6-diisocyanate]]-co-poly[dihydroxy[(oligo-glycolide-ran-ε-caprolactone)-ethylene-(oligo-glycolide-ran-ε-caprolactone)]alt-2,2,4-trimethylhexamethylene 1,6-diisocyanate] of the formula

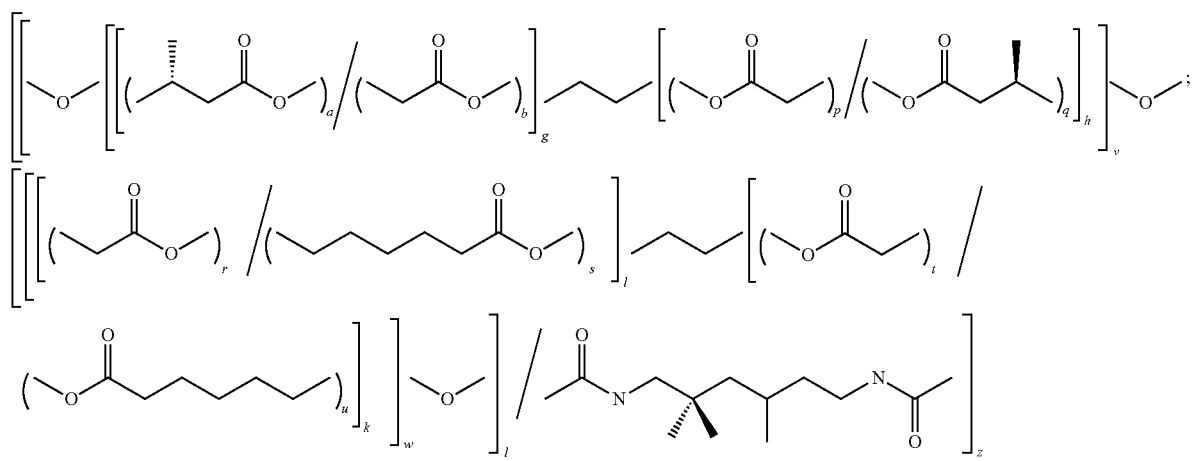

where a=1 to 50, b=1 to 10, p=1 to 10, q=1 to 50, r=1 to 10, s=1 to 50, t=1 to 10, u=1 to 50 and z=1 to 50. Further preferred polymers are identical to the abovementioned with the exception that the glycolide unit of the polymer is replaced by the corresponding lactide or caprolactone.

The block copolymers and diols comprising glycolide units which are particularly preferred are those degradable in five to six days within the human or animal body. Further preferred block copolymers and diols are those whose degradation takes place over months or years. The rate of degradation depends primarily on the number of diglycolide or glycolide units. On storage in a neutral buffer solution at 37° C., the molecular weight decreases with time as a function of the glycolide content. The use of dilactide or caprolactone units does not change the rate of degradability of the polymers of exemplary embodiments of the invention in the body.

Despite the relatively high diglycolide or glycolide/lactide/caprolactone content, the block copolymer of exemplary embodiments of the invention forms phase-segregated crystalline domains in the solid polymer, which decisively determine the mechanical properties of the block copolymer of exemplary embodiments of the invention, such as, for example, the good strength, the brittleness, and the increased ultimate elongation and ultimate tensile stress.

The physical properties of such block copolymers are decisively controlled by the mass ratio of crystalline and amorphous polymer contents. A crystalline content of from 5 to 50% is preferred in this connection. The amount of crystalline component, which has a decisive influence on the mechanical properties, can be chosen relatively freely due to the diol, because the rate of degradation can also be controlled by the diol.

The block copolymers and diols of the invention have exceptionally good solubility in organic solvents such as dioxane, chlorinated solvents, DMSO etc. and have the special advantage that their physical, chemical and biological properties can be adjusted within a wide range through the number of diglycolide/dilactide/caprolactone units. The block copolymers and diols of exemplary embodiments of the invention can thus be adapted for specific uses in each case.

The block copolymers can be modified by copolymerization with further low molecular weight compounds. These copolymerized compounds have one or more functional groups. These functional groups may be protected or unprotected reactive groups, or groups which confer particular use properties on the diols. For example, these low molecular weight compounds may make it possible to use the block copolymers as X-ray contrast agents or in other diagnostic methods such as CT and MRI as agents for increasing contrast. If the functional groups are reactive groups, they make it possible for active substances to be covalently bonded to the block copolymer of exemplary embodiments of the invention. Examples of such active substances are diagnostics such as contrast agents, pharmaceutical active substances, peptides, proteins, etc. Particularly suitable low molecular weight comonomers are diatrizoic acid monoglyceryl ester; 10,11-dihydroxyundecanoic acid; phenacyl 10,11-dihydroxyundecanoate; 2,2-bis(hydroxymethyl)propionic acid; phenacyl bis(hydroxymethyl)propionate. The skilled worker knows how such active substances can be covalently bonded to the diol.

A further important property of the diol of exemplary embodiments of the invention or of the block copolymers is their melt-processibility. They can generally be processed at temperatures between 80° to 200°, preferably between 100° and 150°. Processing can take place correspondingly by known methods by means of extrusion and blow or injection molding. Sheets can also be produced by compression. This melt-processibility entails the advantage for medical implants that the shape and size of the implant can be adapted. A further possibility is for surgical suture material made thereof to be welded appropriately, making it possible to dispense with complicated knotting.

The implants may also be in the form of a tube. The tube may be rigid or flexible. The tubes may have circular, elliptical and polygonal cross sections, it also being possible to dispose a plurality of channels within one tube. It is possible with the implants of the invention to regenerate a functional vessel wall or a nerve. It is possible by a coating with functional vessel cells to avoid a thrombotic occlusion on long-term use, i.e. the biocompatible polymer can in time be replaced by new endogenous cells. The implant material may have a porous structure for particular uses. It may also have a capsule shape to receive pharmaceutical active substances or diagnostics also in the form of particles.

Some uses of the diols of exemplary embodiments of the invention and of the block copolymers in the medical sector are detailed below. Further uses are, of course, possible.

Tubular structures (vessel substitute, trachea substitute, substitute for other biological tubular structures) in firm, coiled, flexible, expandable, self-expanding, braided and knitted form, which may in accordance with the biological and functional requirement have a physically and pharmacologically appropriate texture or coating on the inside or outside. The pharmacological substances are retained either by absorption or covalent chemical bonding to the diol or to the block copolymer. The implant materials are likewise suitable for producing stents (rigid, expandable, self-expanding) for vessels or other biological tubular structures (esophagus, biliary tract, urinary tract).

Sheet-like structures (wound covering, membrane oxygenators, corneal substitute bases etc.) can likewise be produced with the diol of exemplary embodiments of the invention or the block copolymer.

Thread-like structures as surgical suture material and for processing to woven, braided or knitted structures.

Clip-like or clamp-like structures for staplers or clamps for ligating small blood vessels and utilizing the thermoplastic properties for occlusion.

Solid to gelatinous or porous structures as matrix for producing simple or composite biological tissues in vitro (tissue engineering in vivo), use in topical wound treatment.

Preconditioned place holders for skin substitute, adipose tissue, tendons, cartilage and bone, nerves etc.).

Polymeric structures which, owing to the physical or biological loading properties and physical structures (foams, gel, micro- and nanospheres) and the surface structure, make it possible to deliver therapeutic (hormones, medicaments) or cosmetic (liposomes, proteins, vitamins) substances via internal anatomical structures or via the skin.

Compositions of the material of the invention for sclerosing varicoceles, varices of the legs (esophageal varices) or gastrointestinal sources of bleeding (endoscopic or transvascular).

Shaped articles which, in a suitable shape and loading with bioactive substances, make reversible or irreversible contraception possible through blockage (oviduct, spermatic duct).

Artificial auditory ossicles and artificial heart valves, aortas and cardiovascular vessels.

The diol or block copolymer of exemplary embodiments of the invention can additionally be used as base for culturing corneal cells on sheets for transplantation as corneal substitute. In addition, further possible uses in appropriate physical and or biological form are in medical dental, micro- or nanotechnologies.

The diols of exemplary embodiments of the invention are extremely biocompatible in in vitro cell cultures with macrophages and fibroblasts owing to the observation of cell adhesion, cell growth, cell vitality and cell activation, and of the production of extracellular proteins and cytokines.

The polymers of exemplary embodiments of the invention are, apart from in the medical sector, suitable as packaging materials and as building material.

The invention is illustrated further by means of examples below. These examples are intended to be illustrative, and the materials, conditions, and process parameters set forth in these exemplary embodiments are not limiting. All parts and percentages are by weight unless otherwise indicated.

EXAMPLES

Example 1

Preparation of α,ω-dihydroxy[oligo(3-(R)-hydroxybutyrate)-ethylene-oligo(3-(R)-hydroxybutyrate)] by Transesterification of poly[(R)-3-hydroxybutyrate] with ethylene glycol 1055 g of poly[(R)-3-hydroxybutyrate]/BIOPOL (ICI) are dissolved in 3 L of diglyme at 140° C. under $N_2$. Then, 246 g of ethylene glycol and 5.21 g of dibutyltin dilaurate (catalyst) are added. After one hour, 1.5 g (125° C.) and, after a further 2.5 hours, again 1.2 g of catalyst is added. The degradation is followed continuously by GPC measurements and additional 0.6 g of catalyst is added at intervals of 1 hour (h) until the desired molecular weight of the degradation product is reached. The molecular weight is checked by gas phase chromatography (GPC). The degradation is stopped by precipitating the polymer in 10 L of water.

The degraded oligomer is filtered off and suspended in about 6 to 7 L of distilled water a total of 5 times, and filtered off again after 20 hours. After the last washing, the granular oligomer is sucked dry for one hour and then dried in 2 large crystallizing dishes firstly in a drying oven at 50° C. in vacuo. Then, the oligomer is further dried under high vacuum ($10^{-2}$ bar) in a drying oven at 60° C. for 30 hours.

The dry oligomer is subsequently dissolved in methylene chloride to result in a 30-35% solution. The slightly warmed solution is then filtered through a quartz sand bed on a glass filter funnel. The filtrate is purified by chromatography on a silica gel 60 column.

Column height is about 15 cm, and column diameter is 3 cm. The filtrate is concentrated until oligomers start to precipitate at 35° C. The solution (4.5 L) is then poured into 10 L of petroleum ether 30/50 so that the oligomer precipitates.

The precipitate is filtered off and dried.

Yield=86% oligomer ($M_n$=2450).

Example 2

Synthesis of α,ω-dihydroxy[oligo-3-(R)-hydroxybutyrate-stat-glycolide)-ethylene-oligo-(3-(R)-hydroxybutyrate-stat-glycolide)]

The transesterification of α,ω-dihydroxy[oligo-3-(R)-hydroxybutyrate)-ethylene-oligo-(3-(R)-hydroxybutyrate)] with diglycolide was carried out in an oil-heated jacketed 350 ml reactor, which was equipped with a temperature sensor, capillary for nitrogen as protective gas and a reflux condenser on a dropping funnel with pressure equalization. The dropping funnel was packed with A4 molecular sieves. Diglyme or xylenes or other high-boiling inert solvents were used as solvents. The mixture was heated until the required reaction temperature of 140° C. in the reactor was reached. The desired amount of diglycolide was dissolved in dry diglyme and slowly added in the desired amount per unit time by means of a metering pump to the contents of the reactor. The catalyst dibutyltin dilaurate was put into the reactor at the start of the addition of glycolide. The amount of added catalyst was between 0-10% by weight based on the diglycolide. The total reaction time was increased by comparison with the glycolide addition time in some experiments in order to obtain more quantitative glycolide incorporation. The reaction temperature was 140° C., but 130° C. for E7 and 120° C. for E8. After the reaction, the polymer was precipitated in 5 times the amount of n-hexane, filtered off and dried.

Purification of dihydroxy[(oligo-3-(R)-hydroxybutyrate-stat-glycolide)-ethylene-oligo-(3-(R)-hydroxybutyrate-stat-glycolide)]: if the ratio of 3-(R)-hydroxybutyrate units employed in the transesterification to glycolate units falls below a value of about 3, a slight turbidity develops in the reaction mixture towards the end of the transesterification and can be attributed to the production of insoluble oligoglycolides. The polymer can be purified from these parts, the catalyst dibutyltin dilaurate and from diglycolide in the following way:

25 g of crude polymer are extracted with methanol in a SOXHLET with cooling jacket cooling to 18° C. for 6 hours and then dried in vacuo. The polymer is then extracted with dry methylene chloride in the same cooled SOXHLET and precipitated with five times the amount of dry methanol and dried in vacuo.

Yield: 86% of crude polymer.

TABLE 1

Reaction conditions.

| Sample designation | PHB diol [g] | Glycolide [g] | Addition amount [g/h] | Addition amount [%/h] | Addition time [h] | Reaction time [h] | Diglyme [mL] |
|---|---|---|---|---|---|---|---|
| E1 | 20.04 | 2.08 | 0.12 | 5.8 | 17.8 | 23.5 | 170 |
| E2 | 20.04 | 2.08 | 0.17 | 8.2 | 12.0 | 12.0 | 170 |
| E3 | 19.73 | 4.2 | 0.35 | 8.3 | 11.0 | 18.0 | 170 |
| E4 | 20.07 | 6.66 | 0.36 | 5.4 | 18.5 | 18.5 | 170 |
| E5 | 20.04 | 6.64 | 0.3 | 4.5 | 22.0 | 22.0 | 170 |
| E6 | 100.02 | 33.75 | 1.02 | 3.0 | 33.0 | 44.0 | 340 |
| E7 | 150.36 | 50.25 | 1.26 | 2.5 | 40.0 | 62.0 | 400 |
| E8 | 20.8 | 5.4 | 0.34 | 6.8 | 16.0 | 33.5 | 200 |

TABLE 2

Time course of Example 2.

| Sample designation | Time of sampling after start of reaction | Added amount of glycolide based on total [%]* | Maximum 3-(R)-hydroxy-butyrate/glycolate ratio in the polymer | 3-(R)-hydroxy-butyrate/glycolate ratio found in the polymer | Glycolate conversion [%] | Content of transesterified glycolide in blocks of 3 and more units [%] |
|---|---|---|---|---|---|---|
| E8.1 | 6.0 | 40 | 6.2:1 | 22:1 | 20 | 20 |
| E8.2 | 8.5 | 50 | 4.9:1 | 10:1 | 49 | 23 |
| E8.3 | 14.5 | 88 | 2.8:1 | 5.7:1 | 50 | 33 |
| E8.4 | 16.0 | 100 | 2.5:1 | 4:1 | 63 | 47 |
| E8.5 | 33.5 |  | 2.5:1 | 4:1 | 63 | 33 |

Example 3

Preparation of poly[poly[α,ω-dihydroxy[(oligo-3-(R)-hydroxybutyrate-stat-glycolide)-ethylene-oligo-(3-(R)-hydroxybutyrate-stat-glycolide)]alt-2,2,4-trimethyl-hexamethylene 1,6-diisocyanate]]-co-poly[α,ω-dihydroxy[(oligo-glycolide-ran-ε-caprolactone)-ethylene-(oligo-glycolide-ran-ε-caprolactone)]-alt-2,2,4-trimethylhexa-methylene 1,6-diisocyanate]

The polymerization was carried out in an oil-heated jacketed 1000 mL reactor, which was equipped with a temperature sensor, capillary for nitrogen as protective gas and a reflux condenser on a dropping funnel with pressure equalization. The dropping funnel was packed with A4 molecular sieves. The reactor was charged with 400 mL of 1,2-dichloroethane and 31.3 g of dihydroxy[(oligo-3-(R)-hydroxybutyrate-stat-glycolide)-ethylene-oligo-(3-(R)-hydroxybutyrate-stat-glycolide)], $M_n$=2440, product from E7, and heated until the solvent had risen into the condenser and refluxed over the molecular sieves. Refluxing was continued until the solvent had dried to below 20 ppm. Then, 46.25 g of dihydroxy[(oligo-glycolide-ran-ε-caprolactone)-ethylene-(oligo-glycolide-ran-ε-caprolactone)-ethylene-(oligo-glycolide-ran-ε-caprolactone)] $M_n$=1320 (3-(R)-hydroxybutyrate/glycolate=1:1) and 10.01 g of 2,2,4- and 1,4,4-trimethylhexamethylene diisocyanate, mixture of isomers, were added. 100 μl of dibutyltin dilaurate were added as catalyst. The polymerization was carried out at 85° C. for 5 days. During this reaction time, the reaction was followed by GPC and infrared spectroscopy. After the third reaction day, a further 5% by weight of the amorphous diol were added in several steps until the molecular weight remained unchanged and the isocyanate band in the JR had completely disappeared. The polymerization was stopped by precipitating the polymer in five times the amount of cold methanol. The polymer was filtered off and dried in vacuo.

Example 4

Hydrolytic Degradation of poly[poly[α,ω-dihydroxy[(oligo-3-(R)-hydroxybutyrate-stat-glycolide)-ethylene-oligo-(3-(R)-hydroxybutyrate-stat-glycolide)]-alt-2,2,4-trimethylhexamethylene 1,6-diisocyanate]]-co-poly[α,ω-dihydroxy[(oligo-glycolide-ran-ε-caprolactone)-ethylene-(oligo-glycolide-ran-ε-caprolactone)]-alt-2,2,4-trimethylhexamethylene 1,6-diisocyanate] Compared with the Reference Polymer poly[poly[α,ω-dihydroxy[(oligo-3-(R)-hydroxybutyrate)-ethylene-oligo-(3-(R)-hydroxybutyrate]-alt-2,2,4-trimethylhexamethylene 1,6-diisocyanate]]-co-poly[α,ω-dihydroxy[(oligo-glycolide-ran-ε-caprolactone)-ethylene-(oligo-glycolide-ran-ε-caprolactone)]-alt-2,2,4-trimethylhexa-methylene 1,6-diisocyanate]

Glycolide/ε-caprolactone=1/1 molar; PHB/glycolide diol from Example 1.

The influence of the glycolide-modified PHB diol on the rate of degradation was determined in relation to a structurally analogous polymer with unmodified PHB diol. The degradation experiments were carried out on the crude polymer in powder form and on polymer samples, which were previously processed to films and open-cell foams (pore size about 50-300 μm).

Figure 2:
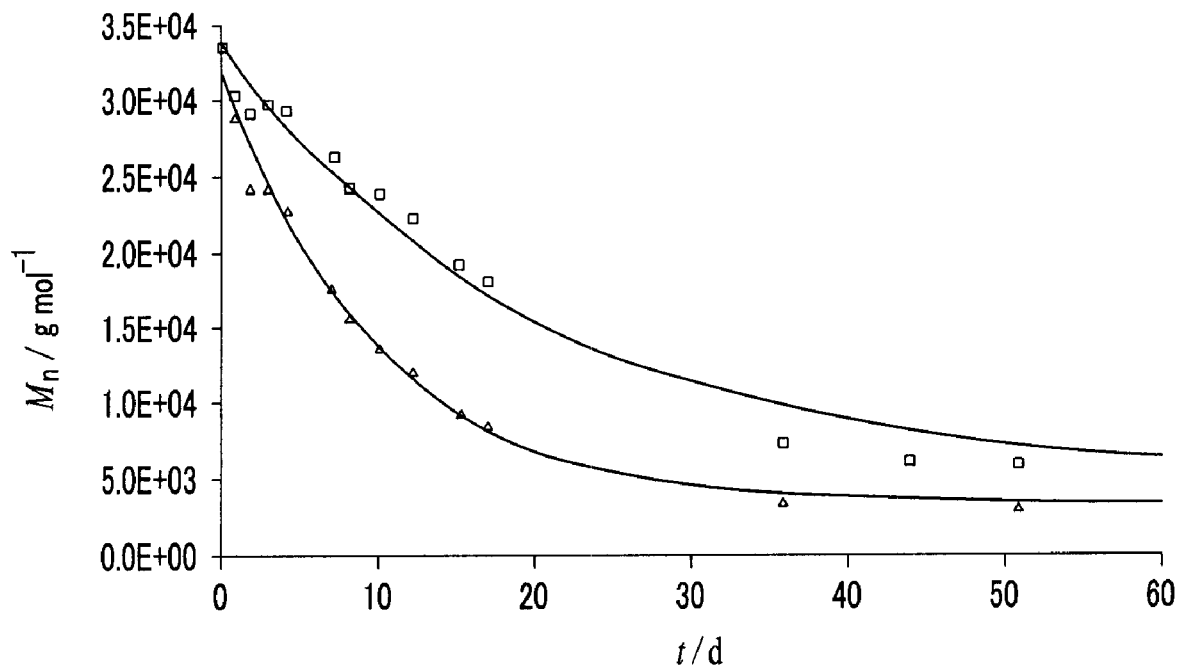

3 foam samples and 3 powder samples plus 20 film samples were made in each case from the polymer of Example 2 and the reference polymer. The initial weights were between 0.1 and 1 g. The samples were stored in 40 ml of distilled water in closable plastic vessels at 37° C. over a period of up to 88 days (d). To prevent the growth of algae, 40 mg of sodium azide were put in each sample. To determine the molecular mass, a small amount of material, in each case foam and powder, was taken alternately from the three flasks at intervals of from one day to three weeks and dried in a vacuum apparatus at room temperature, and the molecular mass was determined by GPC. For the tensile tests, in each case 5 sheets were removed and dried in a vacuum apparatus at room temperature. The film samples were characterized by stress/elongation measurements. In each case, 5 films and foam and powder samples of the initial products were tested at the start of the degradation experiment (FIGS. 1 and 2).

TABLE 3

Decrease in the molecular mass of foam and powder with exponential function as trend line

| Sample designation | Half-life [d] |
|---|---|
| Polymer foam | 8.9 |
| Reference foam | 19.5 |
| Polymer powder | 8 |
| Reference powder | 18 |

It will be appreciated that various of the above-discussed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A biocompatible block copolymer having at least two chemically different block units obtainable by linear polycondensation of (1) a diol with (2) a component selected from the group consisting of the same diol, an α,ω-dihydroxypolyester and an α,ω-dihydroxypolyether, (3) in the presence of an additional compound selected from the group consisting of a diisocyanate, a diacid halide and a phosgene, wherein the diol is obtainable by transesterification of α,ω-dihydroxy-[oligo(3-(R)-hydroxybutyrate)-ethylene-oligo-3-(R)-hydroxybutyrate)] with a compound selected from the group consisting of a diglycolide, a dilactide and mixtures thereof, and wherein the diol has a total content of the diglycolide, dilactide and mixtures thereof of up to 40 mol %, the α,ω-dihydroxypolyester is obtainable by transesterification of poly-(R)-hydroxybutyric acid or copolymers thereof with 3-hydroxyvaleric acid and ethylene glycol, and the α,ω-dihydroxypolyether is selected from the group consisting of α,ω-dihydroxy-poly(oxytetramethylene), α,ω-dihydroxypoly(oxyethylene) and copolymers of ethylene glycol and propylene glycol.

2. The biocompatible block copolymer as claimed in claim 1, wherein the block copolymer is poly[poly[α,ω-dihydroxy-[(oligo(3-(R)-hydroxybutyrate)-stat-glycolide)-ethylene-oligo-(3-(R)-hydroxybutyrate-stat-glycolide)]alt-2,2,4-trimethylhexamethylene 1,6-diisocyanate]]-co-poly[dihydroxy[(oligo-glycolide-ran-ϵ-caprolactone)-ethylene-(oligo-glycolide-ran-ϵ-caprolactone)]alt-2,2,4-trimethylhexamethylene 1,6-diisocyanate].

3. The biocompatible block copolymer as claimed in claim 1, wherein the block copolymer is biodegradable.

4. The biocompatible block copolymer as claimed in claim 1, wherein the block copolymer is degradable in human and animal bodies.

5. The biocompatible block copolymer as claimed in claim 1, wherein the block copolymer is melt-processable.

6. The biocompatible block copolymer as claimed in claim 1, wherein the block copolymer is obtainable by linear co-condensation with further low molecular weight compounds having additional functional groups.

7. The biocompatible block copolymer as claimed in claim 6, further comprising chemically bonded pharmaceutically active substances or diagnostics.

8. A shaped article comprising the biocompatible block copolymer as claimed in claim 1.

9. A medical or veterinary medical implant comprising the biocompatible block copolymer as claimed in claim 1.

10. The implant as claimed in claim 9, wherein the implant has a porous structure.

11. The implant as claimed in claim 9, wherein the implant is in the form of a tube having one or more channels.

12. The implant as claimed in claim 9, wherein the implant is in the form of a heart valve.

13. A surgical aid intended to be fixed in and/or on a human and/or animal body, comprising the biocompatible block copolymer as claimed in claim 1.

14. A diol obtainable by transesterification of α,ω-dihydroxy-[oligo(3-(R)-hydroxybutyrate)-ethylene-oligo-(3-(R)-hydroxybutyrate)] with a diglycolide, and wherein the diol has a total content of the diglycolide of up to 40 mol %.

15. The diol as claimed in claim 14, wherein the diol is α,ω-dihydroxy-[oligo(3-(R)-hydroxybutyrate)-stat-glycolide)-ethylene-oligo-(3-(R)-hydroxybutyrate-stat-glycolide)].

16. A process for preparing a diol, comprising reacting α,ω-dihydroxy-[oligo(3-(R)-hydroxybutyrate)-ethylene-oligo-3-(R)-hydroxybutyrate)] with at least one compound selected from the group consisting of diglycolides, dilactides and mixtures thereof.

17. The process as claimed in claim 16, wherein the reacting is carried out in the presence of a catalyst, and wherein the diol has a total content of the diglycolide, dilactide and mixtures thereof of up to 40 mol %.

18. The process as claimed in claim 16, further comprising dissolving the diol in methylene chloride for purification, and removing impurities.

19. The biocompatible block copolymer as claimed in claim 1, wherein the diol has a total content of the diglycolide, dilactide and mixtures thereof of up to 30 mol %.

* * * * *